(12) United States Patent
Hennings et al.

(10) Patent No.: US 8,685,012 B2
(45) Date of Patent: Apr. 1, 2014

(54) TREATMENT OF CELLULITE AND ADIPOSE TISSUE WITH MID-INFRARED RADIATION

(75) Inventors: David R. Hennings, Roseville, CA (US); David J. Fullmer, Roseville, CA (US)

(73) Assignee: New Star Lasers, Inc., Roseville, CA (US)

(*) Notice: Subject to any disclaimer, the term of this patent is extended or adjusted under 35 U.S.C. 154(b) by 81 days.

(21) Appl. No.: 13/593,458

(22) Filed: Aug. 23, 2012

(65) Prior Publication Data

US 2012/0316547 A1   Dec. 13, 2012

Related U.S. Application Data

(60) Division of application No. 11/847,153, filed on Aug. 29, 2007, now Pat. No. 8,256,429, which is a continuation-in-part of application No. 11/675,028, filed on Feb. 14, 2007, now Pat. No. 8,127,771, which is a continuation-in-part of application No. 11/131,577, filed on May 18, 2005, now Pat. No. 7,217,265.

(51) Int. Cl.
*A61B 18/20* (2006.01)

(52) U.S. Cl.
USPC ............... 606/15; 606/13; 606/16; 607/89

(58) Field of Classification Search
USPC ........ 606/3, 7, 15–18; 607/88–93; 128/88, 89
See application file for complete search history.

(56) References Cited

U.S. PATENT DOCUMENTS

| | | | | |
|---|---|---|---|---|
| 4,848,339 A | * | 7/1989 | Rink et al. | 606/7 |
| 4,868,113 A | | 9/1989 | Jaye et al. | |
| 4,976,709 A | | 12/1990 | Sand | |
| 5,102,410 A | * | 4/1992 | Dressel | 606/15 |
| 5,304,169 A | | 4/1994 | Sand | |
| 5,350,375 A | * | 9/1994 | Deckelbaum et al. | 606/7 |
| 5,445,608 A | * | 8/1995 | Chen et al. | 604/20 |
| 5,647,867 A | * | 7/1997 | Neuberger et al. | 606/15 |
| 5,766,194 A | * | 6/1998 | Smith | 606/167 |
| 5,820,626 A | | 10/1998 | Baumgardner et al. | |
| 5,885,274 A | | 3/1999 | Fullmer et al. | |
| 5,954,710 A | | 9/1999 | Paolini et al. | |
| 5,968,034 A | | 10/1999 | Fullmer et al. | |
| 5,976,123 A | | 11/1999 | Baumgardner et al. | |
| 6,206,873 B1 | * | 3/2001 | Paolini et al. | 606/7 |
| 6,413,253 B1 | | 7/2002 | Koop et al. | |
| 6,443,914 B1 | | 9/2002 | Costantino | |
| 6,451,007 B1 | | 9/2002 | Koop et al. | |
| 6,464,694 B1 | | 10/2002 | Massengill | |

(Continued)

OTHER PUBLICATIONS

U.S. Appl. No. 10/391221, filed Mar. 17, 2003, by Anderson et al.

(Continued)

*Primary Examiner* — Ahmed Farah
(74) *Attorney, Agent, or Firm* — Ray K. Shahani, Esq.; Kin Hung Lai

(57) ABSTRACT

A method and apparatus that will alter the fibrous strands in the fatty layers of the skin to reduce the appearance of cellulite and adipose tissue. Electromagnetic energy is used to selectively shrink or alternatively photoacoustically ablate the collagen in the constricting bands of connective tissue that causes the dimpled appearance of cellulite and adipose tissue while avoiding damage to the surrounding fatty cells.

3 Claims, 14 Drawing Sheets

(56) References Cited

U.S. PATENT DOCUMENTS

| | | | |
|---|---|---|---|
| 6,470,216 | B1 | 10/2002 | Knowlton |
| 6,605,080 | B1 | 8/2003 | Altshuler |
| 6,673,096 | B2 | 1/2004 | Lach |
| 7,217,265 | B2 | 5/2007 | Hennings et al. |
| 7,975,702 | B2 * | 7/2011 | Cho et al. .................. 128/898 |
| 2006/0253112 | A1 * | 11/2006 | Suarez et al. ................. 606/9 |
| 2007/0270788 | A1 * | 11/2007 | Nahen et al. .................. 606/15 |

OTHER PUBLICATIONS

U.S. Appl. No. 10/697,212, filed Oct. 30, 2003, by Hennings et al.
U.S. Appl. No. 10/351,273, filed Jan. 24, 2003, by Baumgardner et al.
U.S. Appl. No. 09/934,356, filed Aug. 21, 2001, by Koop.
U.S. Appl. No. 09/134,776, filed Aug. 1998 by Koop et al.
U.S. Appl. No. 10/738,384, filed Dec. 2003 by Hennings et al.
U.S. Appl. No. 11/131,577, filed May 2005 by Hennings et al.
U.S. Appl. No. 09/185,490, filed Jul. 2000 by Koop et al.
U.S. Appl. No. 09/135,330, filed Jul. 1998 by Koop et al.
U.S. Appl. No. 10/160,579 filed May 2002 by Koop et al.
U.S. Appl. No. 10/031,154, filed Jan. 2005 by Koop et al.
U.S. Appl. No. 08/482,208, filed Jun. 1995 by Hennings et al.
U.S. Appl. No. 08/631,800, filed Apr. 1996 by Hennings et al.
U.S. Appl. No. 10/699,212, filed Oct. 2003 by Hennings et al.
U.S. Appl. No. 351,273 filed Jan. 2003 by Hennings et al.
U.S. Appl. No. 10/335,176, filed Dec. 2002 by Baumgardner et al.
Dr. Michael Olding, "Does Lipo-dissove Work?" published Jun. 28, 2007, www.washingtonpost.com, 7 pages.
Elisa M. Chavez, "In Vitro Study of Photothermal Laser Effects on Bovine Oral Soft Tissue", ISLD 1992, 4 pages.
T. Milner, D. Dave, L. Liew, K. Keikhanzade & J. Nelson, "Evaluation of the Bare Fiber Tip Technique for Cutting Ex-Vivo Human Skin at Two Laser Wavelengths", 3 pages.
U.S. Appl. No. 11/612,324, filed Dec. 2006 by Hennings et al.

* cited by examiner

TREATMENT OF CELLULITE AND ADIPOSE TISSUE WITH MID-INFRARED RADIATION

RELATED APPLICATIONS

This application is a Divisional of related U.S. patent application Ser. No. 11/847,153 filed Aug. 29, 2007 entitled TREATMENT OF CELLULITE AND ADIPOSE TISSUE WITH MID-INFRARED RADIATION, which is a Continuation-In-Part of related U.S. patent application Ser. No. 11/675,028 filed Feb. 14, 2007 entitled TREATMENT OF CELLULITE AND ADIPOSE TISSUE WITH MID-INFRARED RADIATION, which is a Continuation-In-Part of related U.S. Pat. No. 7,217,265 issued May 15, 2007, application Ser. No. 11/131,577 filed May 18, 2005 entitled TREATMENT OF CELLULITE WITH MID-INFRARED RADIATION, which all are incorporated herein by reference in their entireties, and claims any and all benefits to which they are entitled therefrom.

FIELD OF THE INVENTION

This invention relates to a treatment of cellulite and adipose tissue with mid-infrared radiation, and more specifically to a device and system of selectively delivering energy to and thermally altering structures of the skin that cause the dimpled appearance of cellulite and adipose tissue.

BACKGROUND OF THE INVENTION

Cellulite is a condition of the skin characterized by the presence of hard lumps of fatty material surrounded by fibrous connective tissue that gives the skin an orange peel appearance. It is caused by degeneration of subcutaneous blood vessels and results in a thinning of the dermis and pooling of body fluids. In general, adipose tissues is fatty tissue. Cellulite and adipose tissue occurs most often on the thighs, buttocks, and upper arms of Caucasian females and is often associated with obesity.

Current treatments for cellulite and adipose tissue include mechanical massage, exercise, weight loss, diet, and topical drug treatment. None of these treatments are very effective or long lasting. There is a need for a more effective and longer lasting way to smooth the skin of people suffering from cellulite and adipose tissue.

Prior art has focused on damaging or removing the fatty tissue to cure cellulite and adipose tissue. The method may not be effective due to the fact that connecting tissue, not fat, is the true cause of cellulite and adipose tissue. Heating of the fatty cells may be beneficial to a certain degree if the cells are encouraged to metabolize fat faster. However, the appearance as a result of damaged and dead fatty cells is not attractive cosmetically unless the residue is removed in a liposuction therapy.

Other prior art teaches stimulating the generation of new collagen with a variety of optical, electromagnetic, and cosmetic means. U.S. Pat. No. 6,443,914 issued Sep. 3, 2002 to Constantino teaches the use of ultrasound to build additional fibrous tissue through the normal body repair mechanism.

U.S. Pat. No. 6,470,216 issued Oct. 22, 2002 to Knowlton teaches the use of a radio frequency generator to heat and ablate sub-dermal fat and regenerate collagen for skin tightening. RF energy is known to be highly absorbed in fatty tissue, which works in the opposite way to the present invention that avoids melting fat tissue.

U.S. Pat. No. 6,673,096 issued Jan. 6, 2004 to Lach teaches the simultaneous delivery of infrared laser radiation in the range of 650 to 1295 nm and massage devices. It is specifically stated that the objective of the invention is to heat deep layers of tissue and cause lipolysis or decomposition of fatty tissue. This range of wavelengths may heat the fatty tissue but not targeting the connective collagen as in the present invention. In addition, it is not stated that any fluence levels is required and may be trying to perform bio-stimulation with low-level radiation. The present invention clearly requires adequately high fluence levels to shrink or denature collagen and does not require bio-stimulation to be effective.

U.S. Pat. No. 6,605,080 issued Aug. 12, 2003 to Altshuler et al. teaches a method of selectively targeting fatty tissue while avoiding damage to tissue for the purpose of fat removal. The present invention proposes exactly the opposite in order to alter the collagen containing connective tissue, which is the true cause of cellulite and adipose tissue. Altshuler et al. teaches that the optical absorption spectra of fatty tissue is very different from the absorption spectra of surrounding tissue because of the presence of vibrational modes in the molecules of lipids that form fatty tissue. Since both fatty tissue and water based tissue such as collagen can both be found in the same parts of the skin, the difference in these two optical absorption spectra allows a way to selectively target only one of the types of tissue while reducing the heat absorbed by the other; and henceforth preserving it. Altshuler et al. teaches only the ability to heat fat while sparing tissue. Altshuler et al. does not teach that the opposite can be applied under special conditions. Moreover, Altshuler et al. does not mention cellulite and adipose tissue in his work involved with different wavelengths.

U.S. Pat. No. 5,304,169 issued Apr. 19, 1994 to Sand and U.S. Pat. No. 4,976,709 issued Dec. 11, 1990 to Sand teach that collagen goes through several stages of alteration when heated. At temperatures lower or around 50° C., collagen is not affected. At about 60° C., collagen may contract and shrink by about 30% without denaturization or permanent damage to the structure. It has been shown that at these temperatures the shrinkage is long term and the collagen remains viable. At temperatures>65 deg C. however the collagen will denaturize and lose its elasticity and collapse. When this happens to a connective fiber the fiber may weaken, stretch, and possibly break.

U.S. Pat. No. 6,413,253 issued Jul. 2, 2002 to Koop et al., U.S. Pat. No. 6,451,007 issued Sep. 17, 2002 to Koop et al. and U.S. Pat. No. 5,885,274 issued Mar. 23, 1999 to Fullmer et al. teach a mid-IR laser directed to the surface of the skin with energy densities of 10 to 150 J/cm2 and pulse widths of 5 to 500 msec. A pulsed cryogen cooling system is used to protect the epidermis by spraying a burst of R134a cryogen onto the treatment site immediately pre or post laser treatment.

ADVANTAGES AND SUMMARY OF THE INVENTION

The present invention relies on a combination of selective absorption by collagen in fibrous strands or connective tissue and surface cooling to prevent epidermal damage. Strands that are pulling tightly on crevasses in the skin are heated to the point of denaturization, causing them to relax, expand and release the skin outward. On the other hand, strands that connect to outward bulging areas are heated merely to the non-damaging collagen shrinkage temperature of about 65° C. so they permanently contract and help smooth the skin surface.

Lasers in the wavelength region of 1.2 μm to 1.8 μm have been used for many years to shrink and damage collagen for dermatological purposes. Altshuler specifically points out that the result of utilizing a wavelength region of 1.3 μm to 1.6 μm is extremely poor in his fat removal invention because of the poor absorption in fat within the region. Therefore, lasers in the region of 1.3 μm to 1.6 μm are very suitable to be used to selectively shrink or damage collagen in the presence of fatty tissue. The present invention recognizes this fact and combines it in a novel and unique manner with the established good collagen absorption properties of that wavelength region to make a very useful invention. This particular aspect of the present invention accomplishes the opposite of Altshuler.

The selective nature of several bands of infrared electromagnetic radiation allows the collagen to be heated without damage to the surrounding fatty tissue. A combination of selective absorption by collagen in fibrous strands and surface cooling to prevent epidermal damage enables the present invention to work. Strands that are pulling tightly on crevasses in the skin are heated to the point of denaturization, causing them to relax, expand and release the skin outward. On the other hand, strands that connect to outward bulging areas are heated merely to the non-damaging collagen shrinkage temperature of about 65° C. so they permanently contract and help smooth the skin surface.

In particular the Nd:YAG laser, when operated at a wavelength of 1.32 um, is nearly perfect to selectively damage collagen in the presence of fat. Wavelengths longer than 1.6 um will not be able to penetrate deep enough through the epidermal tissue to reach the target depth and wavelengths shorter than 1.3 um do not have enough water absorption to effectively heat the collagen strands. However, when this invention is used in a percutaneous manner utilizing a fiber optic probe, wavelengths such as 2.0 um would be very effective.

The present invention provides a system and method to shrink some of the cellulite and adipose tissue connective strands while weakening and stretching others. Strands in the valleys of the cellulite and adipose tissue dimples are stretched and weakened while strands near the upper hill, top or surface of the dimple are shrunk to pull the top of the dimple inward. Precise control of the heating temperature is critical to accomplish this simultaneously. Radiation fluence must be high (>1 J/cm2) enough to cause permanent shrinkage or denaturization of the collagen in the connective tissue. Low-level fluence (<1 J/cm2) will not work to break connective tissue bonds, but they may stimulate fatty tissue reduction. The improved method to accomplish this is to vary the pulse length of the laser so it will selectively cut or heat and shrink the appropriate target tissue.

The valleys of the cellulite and adipose tissue will be treated at a higher temperature (>70 deg C.) to break the strands and the tops of the hills of the cellulite and adipose tissue will be treated at a lower temperature (50 to 70 deg C.) to shrink the connective strands. The fatty tissue may be heated enough to start to metabolize faster but the selective nature of energy at a wavelength of 1320 nm passes directly through the fat to target (i.e., be absorbed by) the fibrous strands. Also, the fat is useful to maintain a smooth and healthy appearance of the skin, in contradistinction to the teachings of the prior art.

Our new invention uses variable pulse lengths of laser energy to target different structures. Prior to this invention it was not known how to target and damage fibrous strands without causing extensive damage to surrounding tissue. However, by selecting an energy source that matches the transmission bands of fatty tissue and also matches the absorption bands of collagen and simultaneously varies the pulse length of the energy it is now possible to accomplish this. The pulse width of the laser can be adjusted by the use of IGBT devices in the power supply that are able to modulate the current flow to the flashlamp in the laser cavity. The pulse length of the laser can also be modulated by the use of discrete capacitors and inductors in the pulse forming network of the power supply. The most effective pulse lengths for ablation or cutting are in the microsecond region. Preferably 20 to 100 microseconds. This short pulse is capable of generating sufficient peak energies to generate plasma effects or photoacoustic effects at the fiber tip which have been shown to cut and ablate tissue with minimal coagulative side effects.

The most effective pulse lengths for connective tissue shrining or coagulating are in the millisecond region. Preferably 0.5 to 50 milliseconds. These long pulses will not generate plasma effects or photocacoustic effects at the fiber tip but will gently heat and shrink collagen in the connective collagen tissue.

The present invention is utilized inserting a fiber optic energy delivery probe into the skin at the location of the fibrous strands and treating them directly. The use of fiber optic delivery systems for laser energy is well known in the industry, but the use of this technique with a selectively absorbing energy source to treat cellulite and adipose tissue is not obvious. Prior attempts to try this have used energy sources that did not distinguish between the collagen and the fat and the result was extensive damage to all the surrounding tissue and a poor cosmetic result. An additional improvement to this percutaneous approach is to use a fiber optic probe that directs the energy out the front or side of the distal end. This allows the probe to be placed along side the connective strands under the skin and cut in a line with the energy pointed away from the skin surface. It is also possible to perform this procedure under ultrasound imaging to more accurately locate and cut the connective strands. The use of energy in the range of 1.3-1.6 μm or 1.9 to 2.2 μm allows the strands to be cut without affecting the surrounding fatty tissue. In this embodiment the use of the more highly absorbing 2.0-3.0 um radiation such as produced by a Thulium, Holmium, or Erbium doped YAG crystal may be more appropriate as the use of a percutaneous fiber optic makes it unnecessary to optically penetrate the epidermis to reach the target tissue.

Lasers that could be used for this invention include Nd:YAG at 1320 nm, Diode lasers at 1450 nm, ER:Glass laser at 1540 nm, fiber lasers at 1550-1600 nm, Holmium or Thulium lasers at 1.9-2.2 um or Erbium lasers at 2.9 um.

It is yet a further object and advantage of the present invention to provide a method for treating cellulite and adipose tissue by moving the end of the optical fiber past the end of the blunt-end cannula so that heat does not impinge on the needle tip and heat it up. The smooth and blunt end of the cannula, rather than sharpened piercing tip, prevents inadvertent puncture of skin and is safer overall to use. The apparatus includes a relatively stiff or rigid polyimide coated optical fiber, optionally cleaved flat or at an angle, providing the advantage of not requiring the use of the cannula and resistance by the fiber to breakage particularly during placement or use. By extending the firing tip of the fiber optic past the blunt distal end of the cannula, the firing tip is well beyond the cannula and there is no risk of overheating the cannula. The fiber can also be made of sapphire crystal. This material is strong enough to not break in the tissue and can transmit laser wavelengths in the 3 um band such as the Erbium Yag laser at 2.94 um.

The coating is made of a material which absorbs the laser energy at the wavelength utilized. During use, it is an advantage to cause the distal end of the coating to burn to a char during laser delivery. The char heats to a very high temperature and acts as a hot tip ablation device, having a hat, ablative cutting surface. In an embodiment of the present invention, the method using a pulsed laser in conjunction with a coated fiber such that the rapid temperature rise at the charred fiber tip causes an acoustic explosion which ablates and disrupts tissue.

The fiber can be inserted beyond or past the end of the cannula tip so that it is no longer adjacent the tip, increasing maneuverability and improving the efficiency of the cutting tip. Additionally, by moving the distal tip of the optical fiber well past the tip of the cannula there is less chance that the metal cannula will be heated by the laser beam exiting from the emitting face of the fiber, it provides an advantage to minimize heating of the tip of the cannula which if heated may cause burns to the patient's skin as it is introduced and/or withdrawn before, during or after use.

It is also an object and advantage of the invention to use a Touhy Borst clamp on the fiber as a marker to guarantee that the fiber is well beyond the cannula tip. Using an aiming beam up to 10 times or more brighter than the conventional aiming beam, the practitioner can easily determine exactly where the fiber tip is and be able to move it well past the cannula tip before firing it to ablate the undesirable connective tissue.

Further objects and advantages of the present invention will be come apparent through the following descriptions, and will be included and incorporated herein.

DETAILED DESCRIPTION OF THE EMBODIMENT

Figure 1:
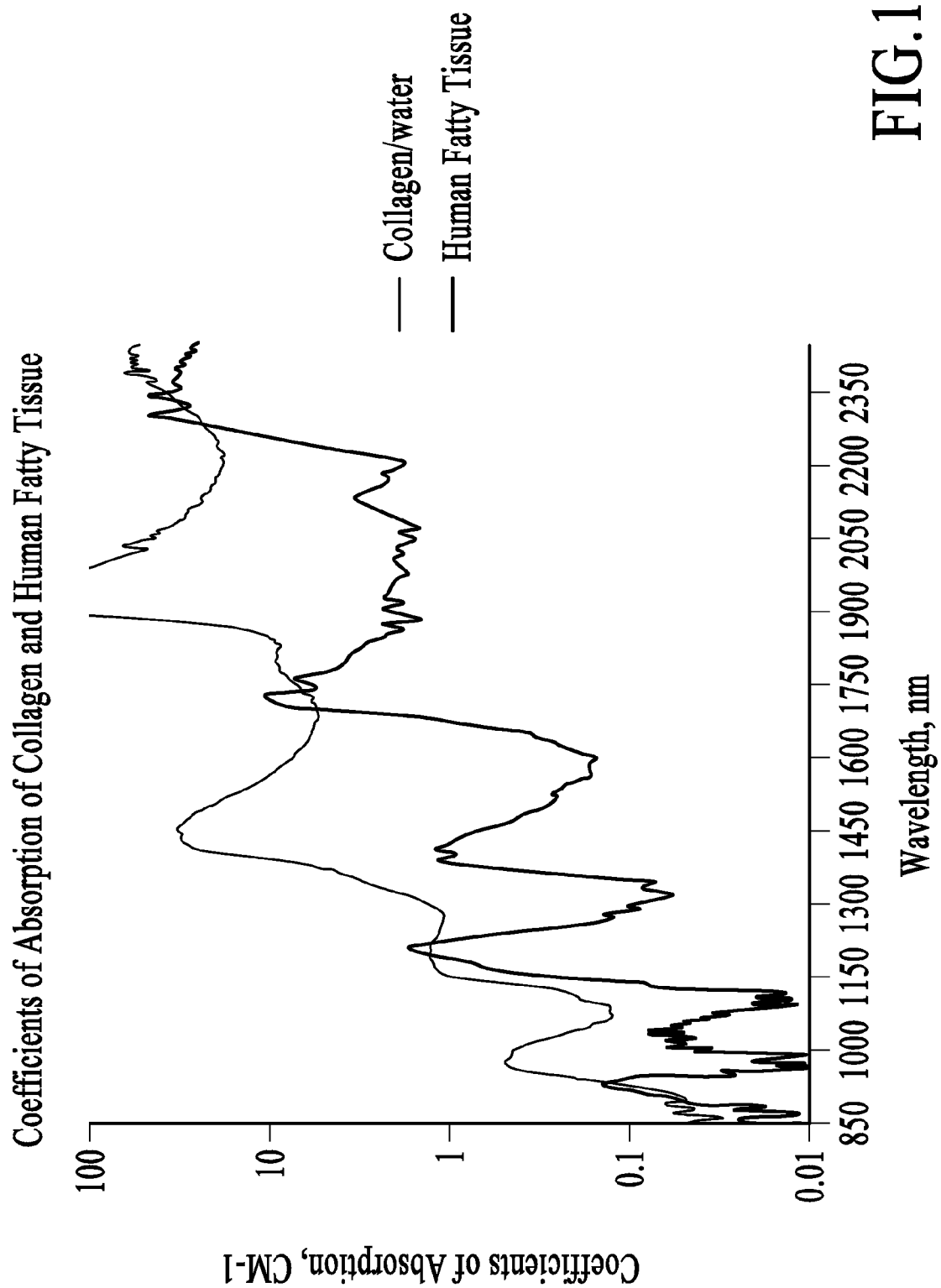
FIG. 1 is a graph illustrating the infrared absorption curves of collagen/water and human fatty tissue 124.

The description that follows is presented to enable one skilled in the art to make and use the present invention, and is provided in the context of a particular application and its requirements. Various modifications to the disclosed embodiments will be apparent to those skilled in the art, and the general principals discussed below may be applied to other embodiments and applications without departing from the scope and spirit of the invention. Therefore, the invention is not intended to be limited to the embodiments disclosed, but the invention is to be given the largest possible scope which is consistent with the principals and features described herein.

It will be understood that in the event parts of different embodiments have similar functions or uses, they may have been given similar or identical reference numerals and descriptions. It will be understood that such duplication of reference numerals is intended solely for efficiency and ease of understanding the present invention, and are not to be construed as limiting in any way, or as implying that the various embodiments themselves are identical.

DEFINITIONS

An "absorption coefficient" of a substance is a measure of the fraction of incident light that is absorbed when light is passed through the substance. The absorption coefficient (typically in units of cm.sup.−1) varies with the nature of the absorbing substance and with the wavelength of the light.

"Collagen" as used herein refers to any of the several types of collagen.

Collagen biosynthesis is said to be "inhibited' when cells treated with the claimed methods secrete collagen at a rate that is less than about 70% of that of untreated cells. Preferably, treated cells secrete collagen at a rate that is less than about 50%, and more preferably less than about 30% of the rate at which untreated cells secrete collagen.

Collagen biosynthesis is said to be 'stimulated' when cells treated with the claimed methods secrete collagen at a rate that is greater than about 110% of the rate at which untreated cells synthesize collagen. Preferably, treated cells secrete collagen at a rate that is about 150%, and more preferably greater than about 200% greater than that of untreated cells.

"Monochromatic" light is of one wavelength or a narrow range of wavelengths. If the wavelength is in the visible range, monochromatic light will be of a single color. As used herein, "monochromatic" refers to light that has a bandwidth of less than about 100 nm. More preferably, the bandwidth will be less than about 10 nm, and most preferably less than about 1 nm.

"Non-coherent light energy" is light that is non-laser. Unlike laser light, which is characterized by having its photon wave motions in phase, the wave motions of the photons that make up non-coherent light are in a randomly occurring phase order or are otherwise out of phase.

A "wound" as used herein, refers to any damage to any tissue in a living organism. The tissue may be an internal tissue, such as the stomach lining or a bone, or an external tissue, such as the skin. As such, a wound may include, but is not limited to, a gastrointestinal tract ulcer, a broken bone, a neoplasia, and cut or abraded skin A wound may be in a soft tissue, such as the spleen, or in a hard tissue, such as bone. The wound may have been caused by any agent, including traumatic injury, infection or surgical intervention.

A "growth factor" as used herein, includes any soluble factor that regulates or mediates cell proliferation, cell differentiation, tissue regeneration, cell attraction, wound repair and/or any developmental or proliferative process. The growth factor may be produced by any appropriate means including extraction from natural sources, production through synthetic chemistry, production through the use of recombinant DNA techniques and any other techniques, including virally inactivated, growth factor(s)-rich platelet releasate, which are known to those of skill in the art. The term growth factor is meant to include any precursors, mutants, derivatives, or other forms thereof which possess similar biological activity(ies), or a subset thereof, to those of the growth factor from which it is derived or otherwise related.

FIG. 1 is a graph illustrating the infrared absorption curves of collagen/water and human fatty tissue 124. The graph illustrates the coefficient of absorption (CM-1) of collagen and of human fatty tissue 124 as a function of wavelength respectively. As shown in FIG. 1, the optical absorption spectra of fatty tissue 124 is very different from that of collagen because of the presence of vibrational modes in the molecules of lipids that form fatty tissue 124. The coefficient of absorption of human fatty tissue 124 is extremely low in the wavelength region of 1.3 µm to 1.6 µm indicating poor absorption in fat within the region. The peak coefficient of absorption of fatty tissue 124 absorbing bands are 0.90µ-0.93 µm, 0.119 µm-0.122 µm, and 0.17 µm-0.173 µm. However, as also shown in FIG. 1, the coefficient of absorption of water-based collagen is relatively high in the wavelength region of 1.3 µm to 1.6 µm indicating good infrared absorption. The system 100 of present invention combines this understanding with the established high coefficient of absorption of collagen in that wavelength region. Therefore, lasers having output in the region of between about 1.3 µm and about 1.6 µm and between about 1.9 um and about 2.2 um are very suitable to selectively shrink or denaturize collagen containing connective tissue 122 in the presence of fatty tissue 124.

Figure 2:
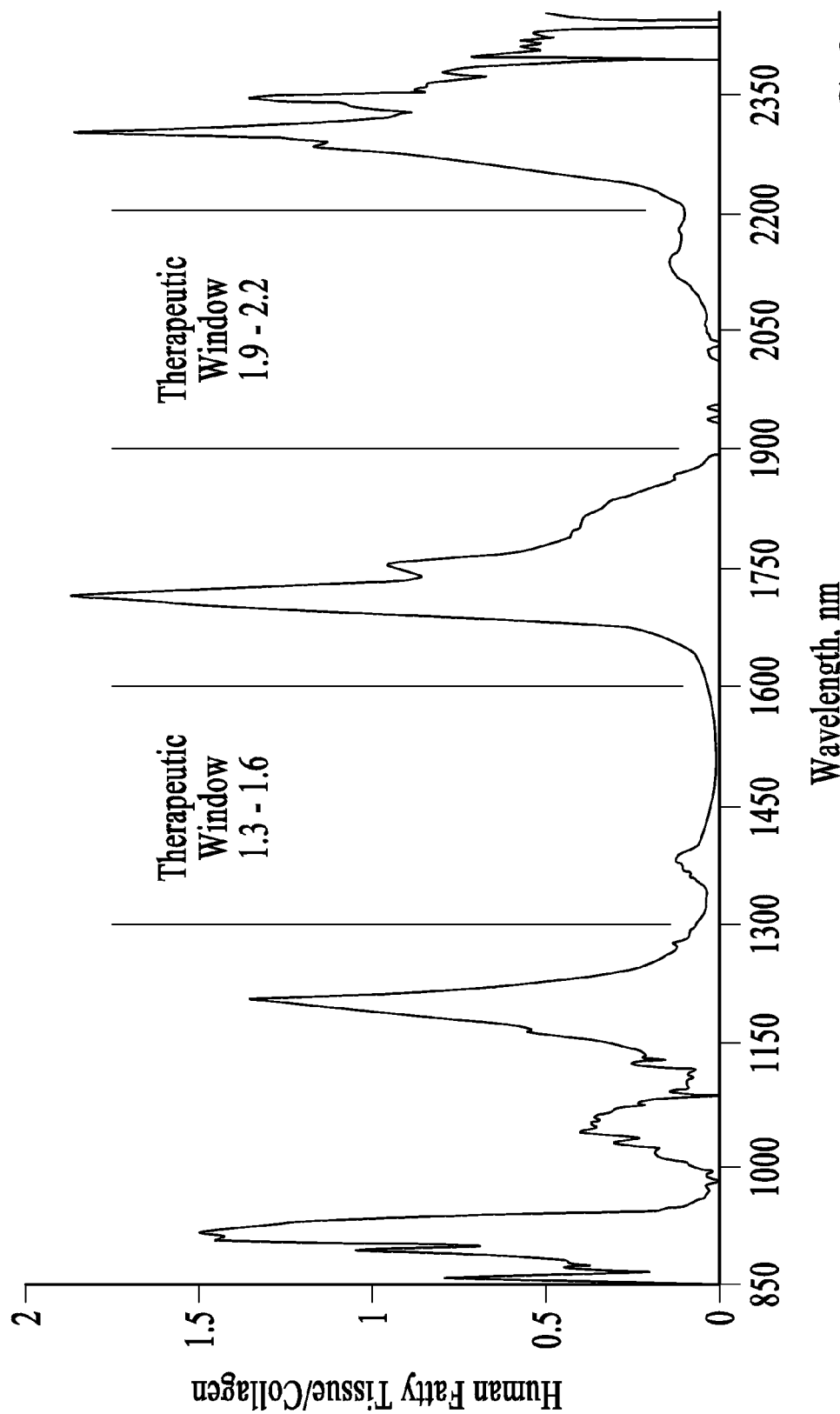
FIG. 2 is a graph illustrating the ratio of the coefficients of infrared absorption of human fatty tissue 124 and collagen as a function of wavelength.

FIG. 2 is a graph illustrating the ratio of the coefficients of infrared absorption of human fatty tissue 124 and collagen as a function of wavelength. As indicated, the higher the ratio, the larger the difference between infrared absorption of fatty tissue 124 and that of collagen; and vice versa. As shown in FIG. 2, there are windows where the ratio between fatty tissue 124 and collagen is the lowest, these are called "therapeutic windows". "Therapeutic windows" indicate the range of wavelengths where collagen containing connective tissue 122 may be effectively targeted with minimal damage to fatty tissue 124. As shown in FIG. 2, these windows occur in the wavelength range of 1.3 µm-1.6 µm and 1.9 µm-2.2 µm respectively. Wavelengths around 3 um are highly absorbed in both fat and tissue and can be used to cut tissue located directly in front of the fiber probe.

Operation of System to Modulate Laser Pulse Widths

Figure 3:
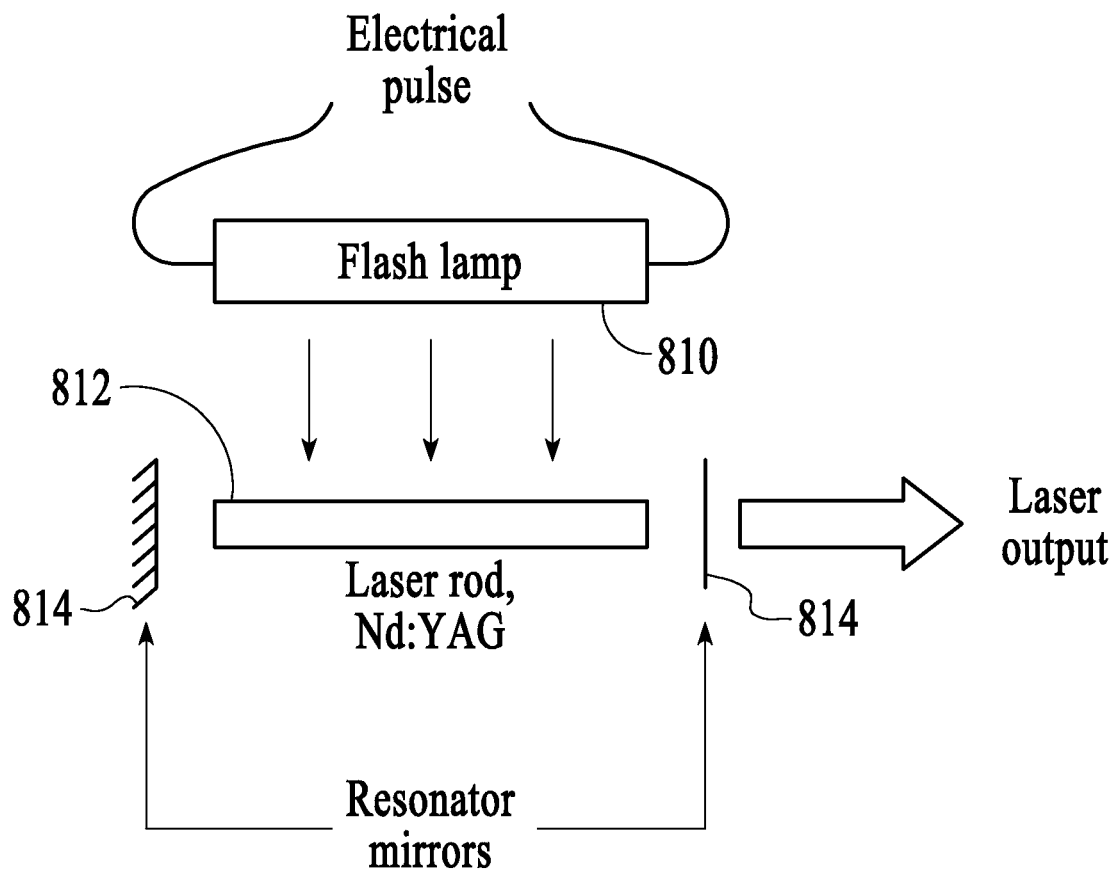
FIG. 3 is a schematic representation of a flashlamp pumped solid state laser.

FIG. 3 is a schematic representation of a laser that utilizes a flashlamp to pump the laser crystal. The use of a flashlamp is method of laser pumping that is generally known to those skilled in the art. It was one of the first methods used to produce laser energy, and is still in wide use because of it low cost and ability to produce large amounts of pulsed energy. The method described herein is a standard way to produce pulsed energy from a solid state laser such as an Nd:YAG or other crystalline medium laser. This method has been taught for many years for other applications, but is adapted to produce the type of laser output used by the methods described herein. The prior art applications utilize continuous output semiconductor lasers that do not utilize flashlamp pumping. Semiconductor or diode lasers are activated by directly stimulating the medium with a low voltage direct current and, by design, cannot store and output giant energy pulses. The exemplary power supply described below is intended to illustrate a technique that is used to produce pulsed laser operation and to show that it is fundamentally different from continuous laser operation for the present methods.

A pulsed laser flashlamp 810 is a tube of glass or quartz that is sealed off at each end and contains a rare gas such as Xenon or Krypton. Electrical contacts through each end connect to an anode and a cathode inside the glass tube. When a high voltage is applied to the ends of the lamp it will discharge with a broad band white light. The lamp is placed in close proximity to the lazing crystal 812 so that the crystal absorbs the light energy. The crystal 812 stores this energy until a lazing threshold is reached when the energy is emitted through a process called stimulated emission. A set of aligned mirrors 814 around the crystal 812 allows selection of the wavelength and direction for this energy to propagate and to be coupled out of the crystal 812. Lasers that can be operated in giant pulse mode require lazing mediums that can store and then selectively release large amounts of energy. Solid state crystal lasers such as Nd:YAG lasers are optimal for this purpose. Semiconductor or diode lasers do not store significant amounts of energy and therefore can only be operated in continuous or very low energy per pulse modes.

Figure 4:
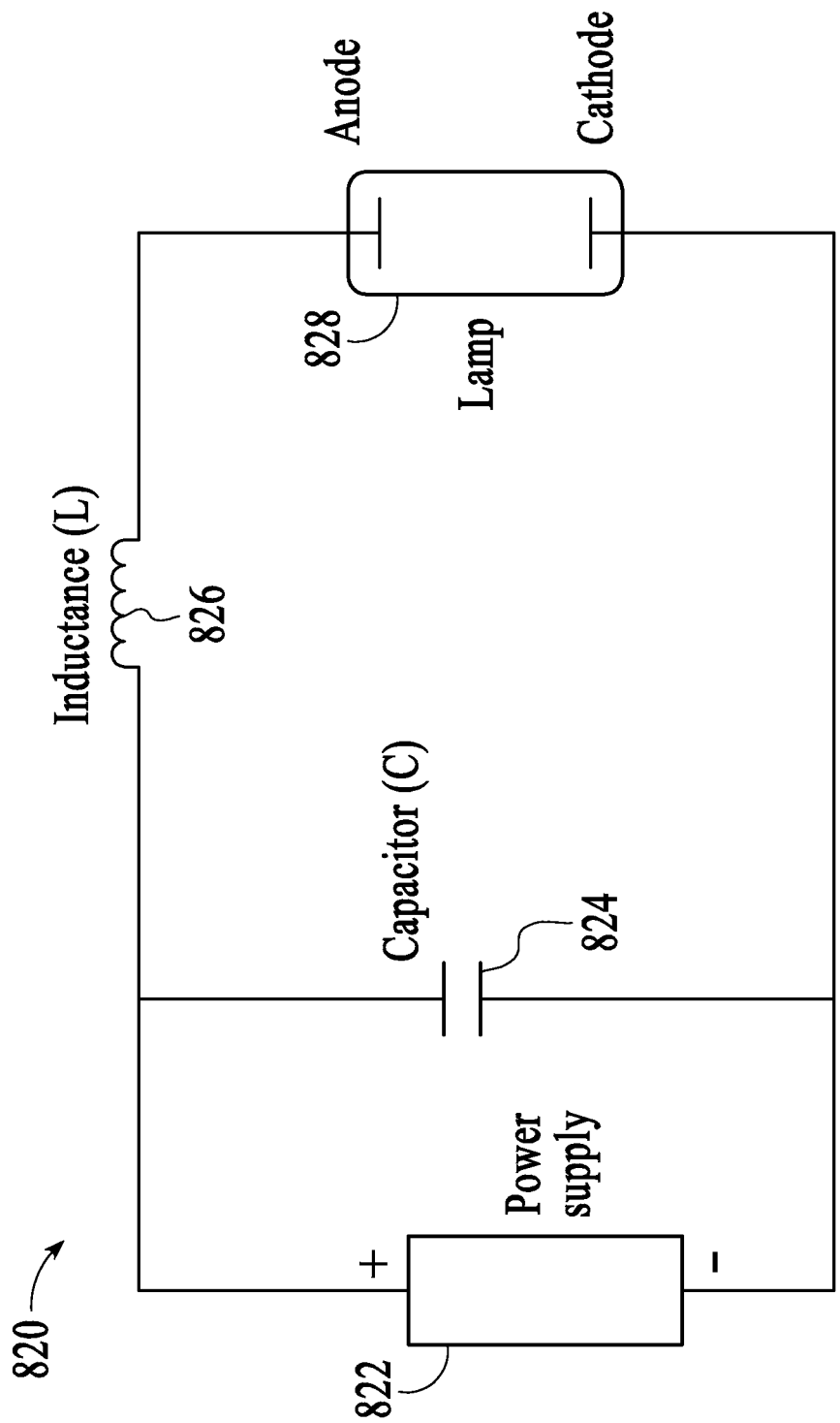
FIG. 4 is a schematic representation of an electronic pulse forming network used to produce pulsed laser output.

FIG. 4 is a schematic representation of a power supply 820 that can be used to pulse the flashlamp 810 to produce large energy pulses used in the methods described herein. A pulse lamp driving circuit typically contains a high voltage power supply 822, a main storage discharge capacitor 824, an inductor 826 to match lamp impedance and to control the pulse length, a lamp 828, and a triggering mechanism, such as a trigger transformer 852 described below in relation to FIG. 6, to initiate ionization in the gas in the lamp so that the main discharge current can flow through the lamp.

When the lamp 828 is non-ionized, it has a very high impedance and thus initially all the power supply current flows into the capacitor 824. If the voltage across the capacitor 824 or the trigger circuit reaches a value equal to the breakdown voltage of the lamp 828, ionization of the lamp 828 gas starts to occur and its impedance begins to fall. If sufficient charge is available, the plasma of ionized gas in the lamp 828 completely fills the bore and the lamp radiates energy in the form of light. Eventually all of the energy in the capacitor 824 is expended and the lamp 828 returns to a de-ionized state. This process can be repeated with a repetition rate that can be from a single isolated pulse to thousands of times every second. The energy discharges from the capacitor 824 through the flashlamp 828 with a pulse length that is determined by the values of the capacitor 824 and inductor 826 that has been selected for the pulse forming network. This pulse length can be shown to be: $T = \frac{1}{3}(LC)^{1/2}$, where L is the value of the inductor 826 and C is the value of the capacitor 824 in the network.

Figure 5:
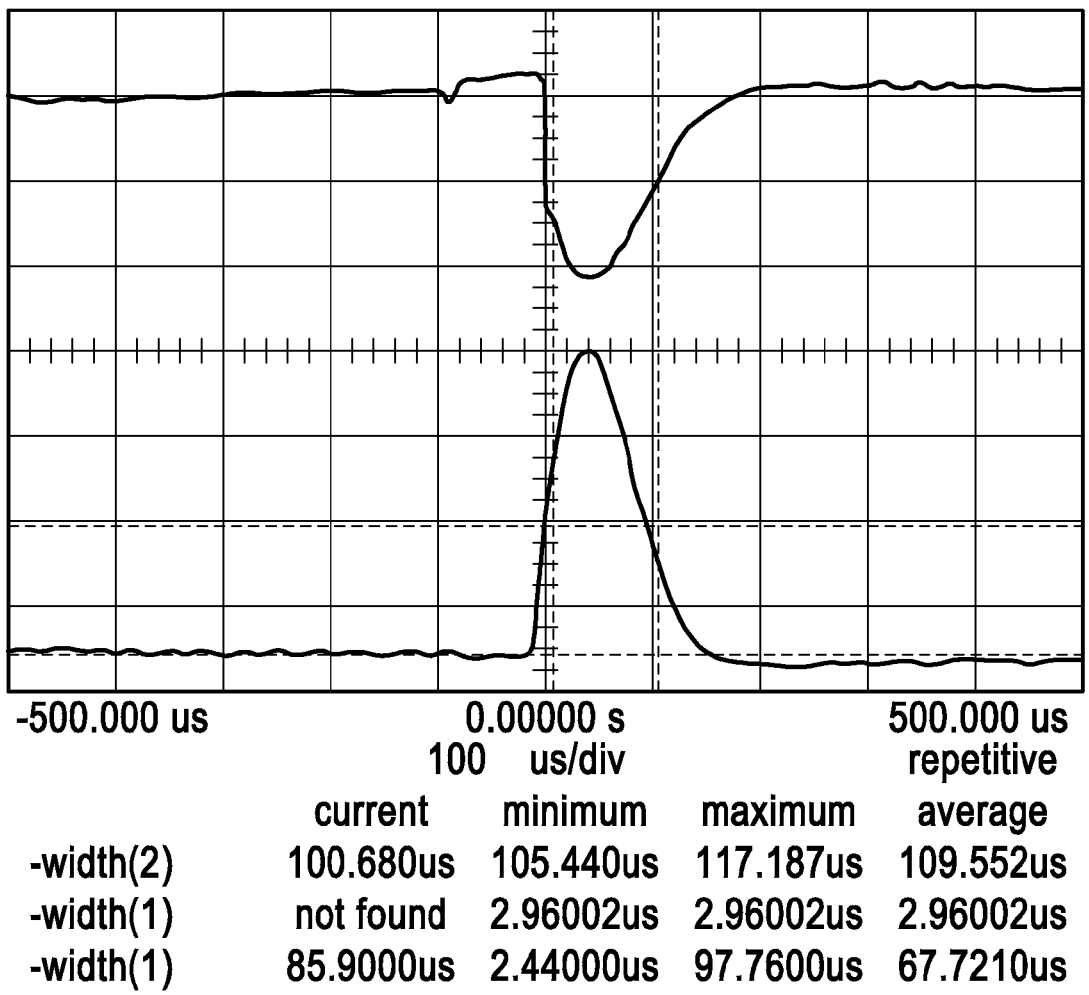
FIG. 5 is a photo of an oscilloscope readout illustrating a flashlamp pulse generated by the pulse forming network shown in FIG. 4.

Since the crystalline laser medium 812 will absorb white light and emit coherent monochromatic light in close agreement with the flashlamp pulse, proper selection of the flashlamp pulse length provides a method for controlling the giant pulse length of a solid state laser. It is controlled by the choice of the value of the main discharge capacitors 824 and inductors 826. However, the laser operates most efficiently when the flashlamp pulse length closely matches the fluorescent lifetime of the lasing medium and when the PFN (pulse forming network) matches the impedance of the lamp 828. For a typical Nd:YAG laser, this is about 200 µseconds. FIG. 5 is a photo of an oscilloscope readout illustrating an exemplary flashlamp pulse generated by the pulse forming network shown in FIG. 4.

The energy per pulse is determined by the energy stored in the main capacitor. This energy can be calculated to be: $E = \frac{1}{2}C(V)^2$, where V is the voltage that the capacitor is charged to. The output lasing energy will be a percentage of the flashlamp pump energy within the cooling constraints of the rest of the laser. For Nd:YAG crystals usually about 3% of the pump energy emits as coherent laser energy.

For the present endovenous laser treatment methods, typical values for the components are:

C=10 to 1000 μFarads
L=10 to 5000 μHenrys
V=200 to 2000 volts

These values can produce pulse lengths from 3 to 800 μseconds, pump energies from 0.2 Joules to 2000 Joules per pulse, and laser output energies of 6 millijoules to 60 joules per pulse. These values have been shown to be effective in reducing the coagulum that develops at the tip of an endovenous laser fiber during treatment.

Figure 6:
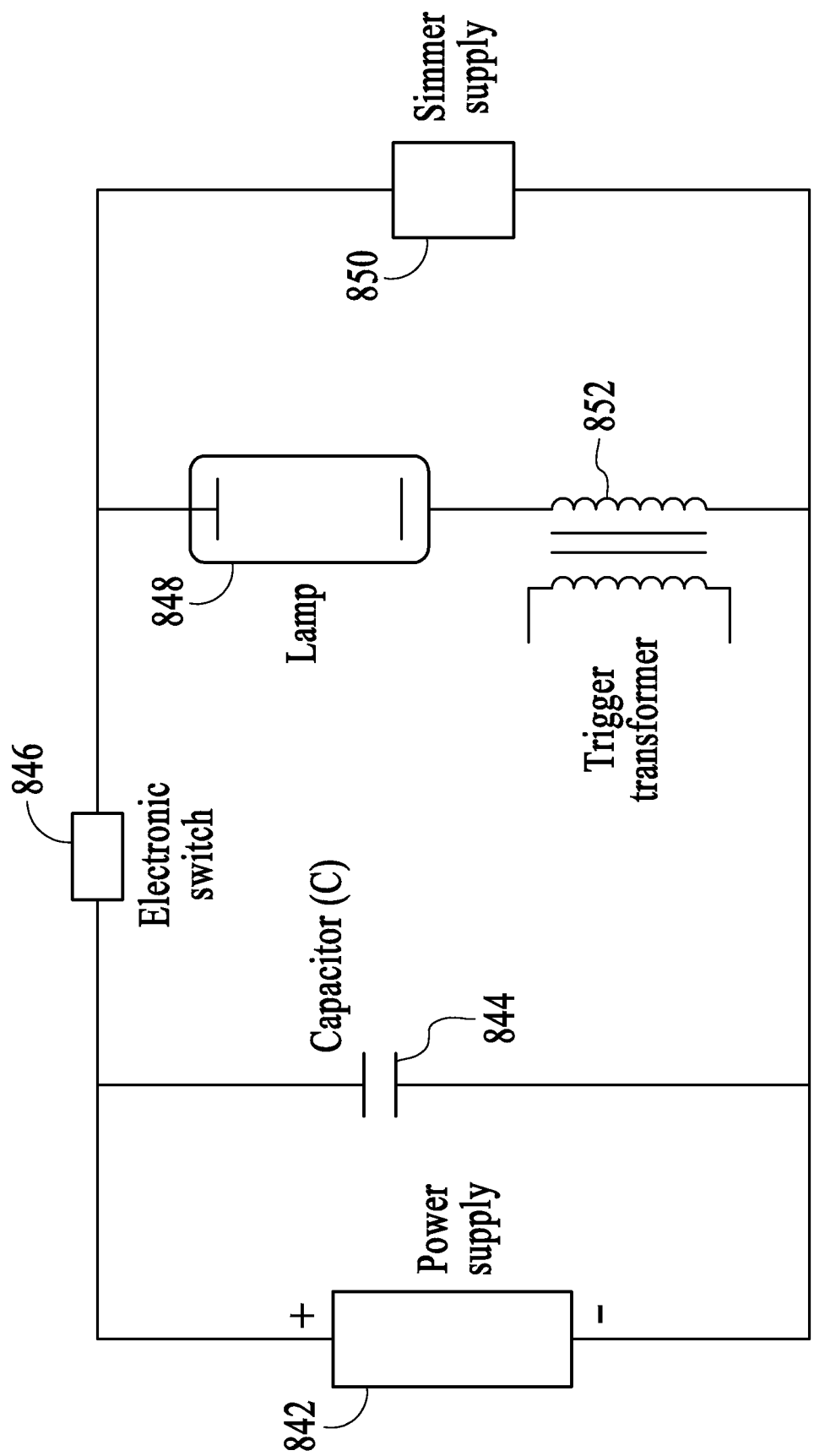
FIG. 6 is a schematic representation of an Isolated Gate Bipolar Transistor (IGBT) system suitable for producing pulsed laser output.

FIG. 6 illustrates an alternative electronic switching device referred to as an IGBT (Isolated Gate Bipolar Transistor), which can be used to generate pulsed energies in a flashlamp of the same values as a capacitive, inductive pulse forming network. The IGBT circuit includes a high voltage power supply 842, a main storage discharge capacitor 844, an electric switch 846, a lamp 848, a simmer supply 850, and a trigger transformer 852 to initiate ionization in the gas in the lamp so that the main discharge current can flow through the lamp. The device shown in FIG. 6 is usually operated at a fixed capacitor voltage and controls the energy discharge into the flashlamp by controlling the pulse length of the discharge. The IGBT device can shut off the current at any time, as opposed to a conventional transistor which cannot be controlled once it is turned on. A trigger transformer 852 is used to strike a high voltage arc in the flashlamp 848 to initiate a plasma current in the lamp of about 100 mamps. This plasma is maintained by a current limiting power supply called a simmer supply 850 and allows the discharge of a high current flashlamp pulse controlled by the IGBT 846.

For endovenous laser treatment methods, typical values for the capacitor 844 and voltage 842 to control flashlamp pulses are:

C=1000 to 30,000 μFarads
V=100 to 500 volts

Figure 7A:
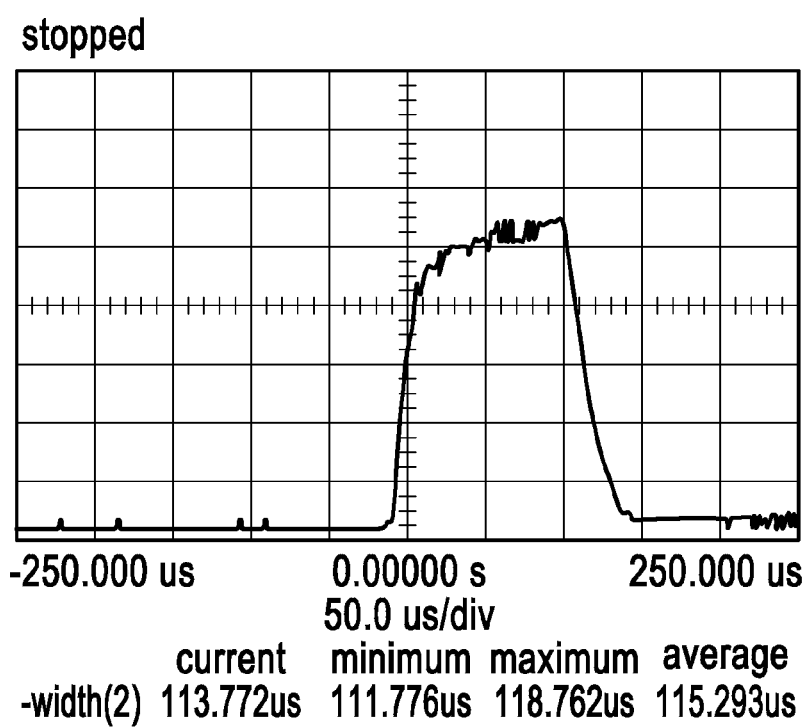
FIGS. 7A, 7B and 7C are photos of an oscilloscope readout illustrating flashlamp pulses produced by the IGBT system of FIG. 6.
Figure 7B:
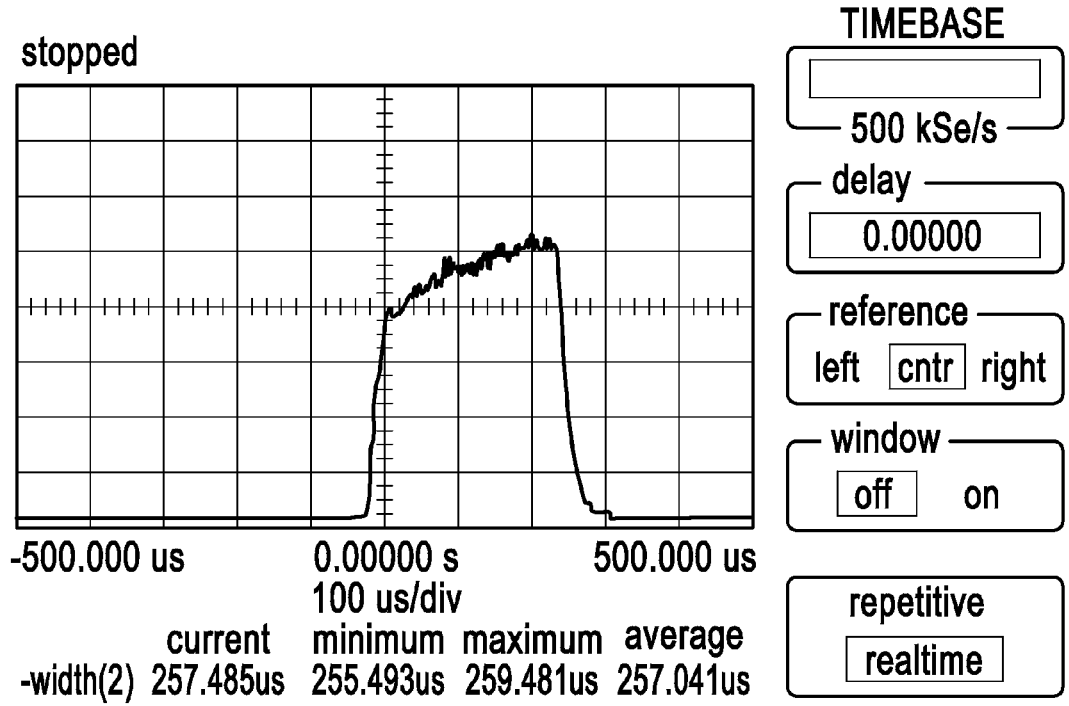
Figure 7C:
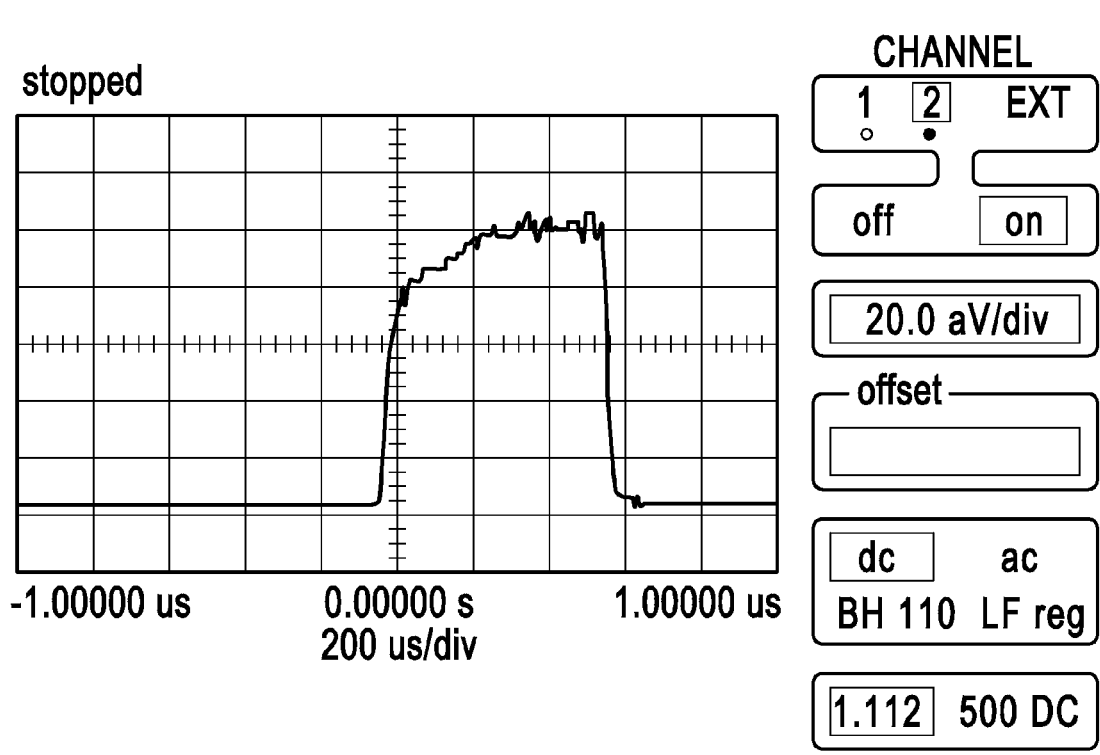

These values can produce pulse lengths from 1 to 5000 μseconds, pump energies from 0.2 to 2000 joules per pulse, and laser output energies from 6 millijoules to 60 joules per pulse. FIGS. 7A-C are photos of oscilloscope readouts illustrating exemplary flashlamp pulses produced by the IGBT system of FIG. 6. For example, FIG. 7A illustrates a pulse length of about 110 μseconds, FIG. 7B illustrates a pulse length of about 250 μseconds, and FIG. 7C illustrates a pulse length of about 550 μseconds.

Those skilled in the art will recognize that there are other available methods to pulse lasers, but that the two methods described herein utilizing flashlamp pulse sources represent efficient and effective methods for producing high energy short pulses that are sufficient to vaporize blood coagulum formed at the tip of a fiber optic catheter in a blood vessel. Other laser pulse methods include the use of optical switches such as Pockels Cells or saturable dyes that bleach when intracavity energy densities exceed a calculated minimum. These methods produce very short pulses that can easily damage fiber optic delivery devices and are not preferred. It is also possible to mechanically shutter a continuous laser, but this would result in a very large and inefficient laser in which over 90% of the laser output would be wasted.

Figure 8:
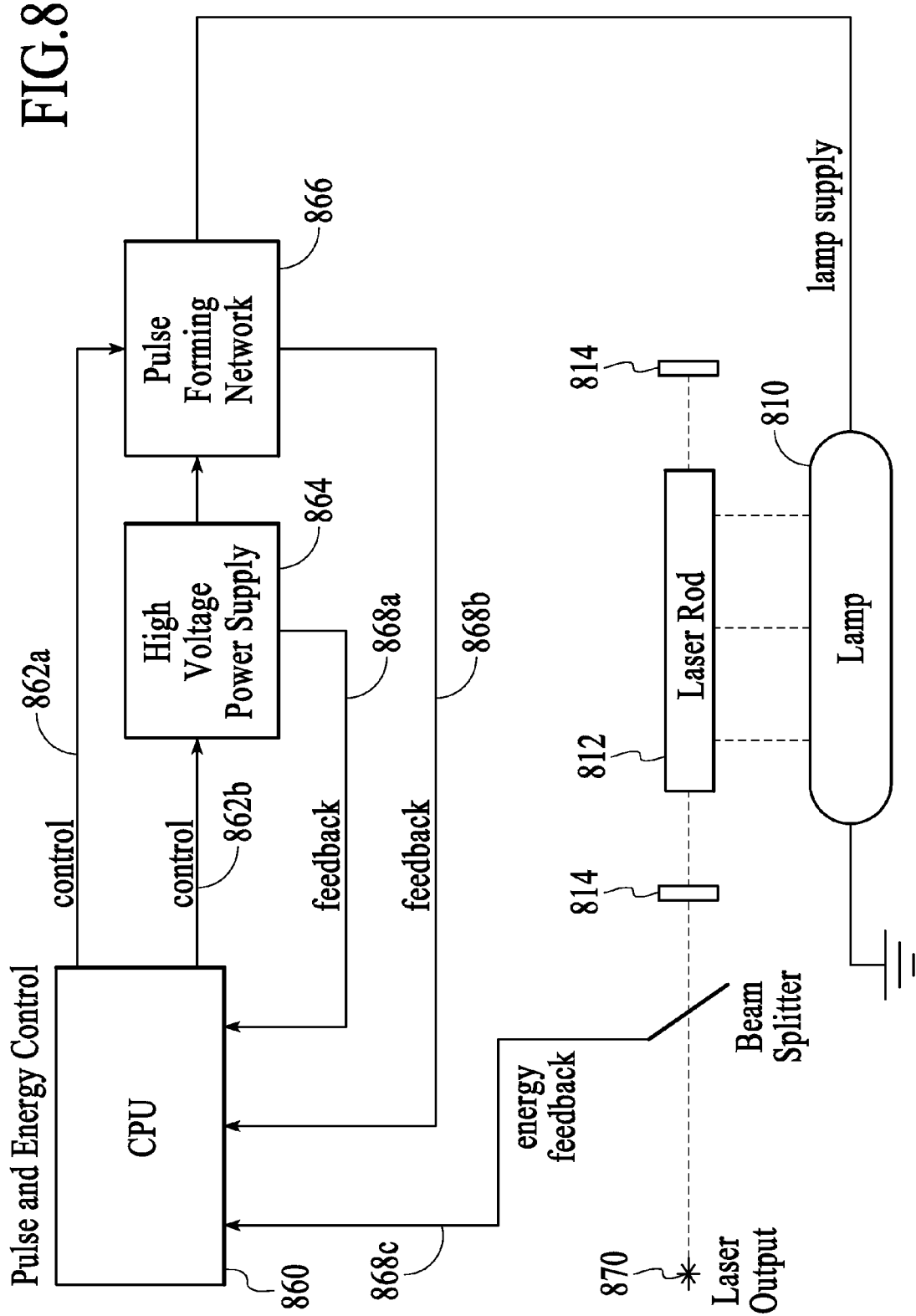
FIG. 8 is a schematic representation of a control system suitable for producing pulsed laser output.

FIG. 8 is a schematic representation of the controls needed to modify the pulse length and energy of a flashlamp pulsed laser. The energy and repetition rate of the pulsing is selected on a control panel attached to a central processing unit (CPU) 860. The CPU 860 sends control signals 862a-b to the high voltage power supply 864 and the pulse forming network 866 or electronic switch to select pulse energy and width. After each pulse, feedback signals 868a-c from the high voltage power supply 864, the pulse forming network 866, and the laser output 870 are routed back to the CPU 860 and compared for the correct energy and pulse. Energy and pulsing are thereby controlled on a real time basis.

Collagen goes through several stages of alteration when heated. At temperatures lower or around 50° C., collagen is not affected. At about 60° C., collagen may contract and shrink by about 30% without denaturization or permanent damage to the structure. It has been shown that at these temperatures the shrinkage is long term but the collagen remains viable. At temperatures greater than 65° C. however the collagen will denaturize and lose its elasticity and simply collapse. When this happens to a collagen containing connective fiber 122, the connective tissue 122 may weaken, stretch, and possibly break.

A principle of treatment system 100 of the present invention is to selectively shrink some of the cellulite connective tissue 122 while weakening and stretching others; all while neighboring fatty tissue 124 is avoided. As shown best in FIG. 9, multiple bursts of pulsed energy 504, which is ultimately from appropriate energy source 102 that compares and optionally matches the transmission bands of fatty tissue 124 and the absorption bands of collagen, are directed to target tissue 120. The pulsed energy 504 heats up connective tissue strands 122 in the valleys 510 of the cellulite and adipose tissue dimples to the temperature range of 70° C. plus so they are stretched and weakened. At the same time, connective tissue strands 122 comprising the hill top surface 512 of the cellulite and adipose tissue dimples are heated to the temperature range between 50° C. and 60° C. so they are shrunk to a certain degree. As a result, there is an inward pull in the direction indicated as F generated at the top of the dimples 512, collectively the appearance of cellulite and adipose tissue is eliminated and skin surface 116 is smoothed. The fatty tissue 124 may be heated enough to start to metabolize faster but the selective nature of laser energy 504 such as Nd:YAG at 1.32 μm will allow most of the energy to transmit directly through the fat tissue 124 to target the collagen containing connective fibrous strands 122. Also, the fat tissue 124 is needed to maintain a smooth and healthy appearance of the skin. As opposed to methods and systems of the prior art, fatty tissue 124 is spared during cellulite and adipose tissue treatment of the present invention.

Figure 9:
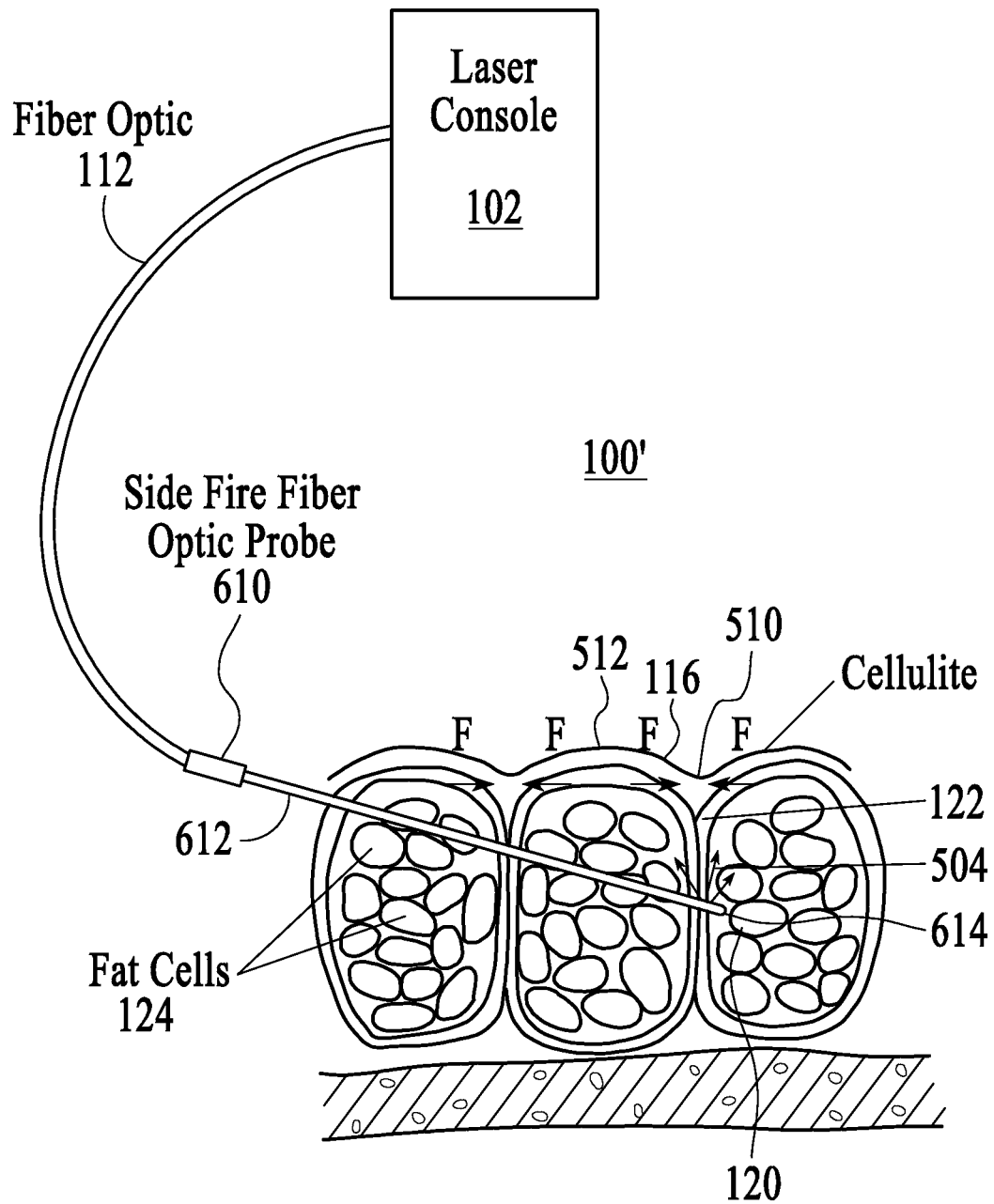
FIG. 9 is a representative detail schematic diagram of an embodiment of the cellulite and adipose tissue treatment system 100' of the present invention.

FIG. 9 is a representative detail schematic diagram of an embodiment of the cellulite and adipose tissue treatment system 100 of the present invention. As shown, the laser energy 110 from the energy source 102 is directed into delivery device 112 which may be a fiber optic, articulated arm, or an electrical cable etc. At the distal end of delivery device 112 is a front or side fire fiber optic probe 610 for directing the laser energy 504 inside the target tissue 120. The front or side fire fiber optic probe 610 includes a long cannula 612 for easy access and a forward or side-firing tip 614 for safe treatment, which may optionally comprise mechanical breaking of the fibers when in contact.

In one embodiment, a fiber optic probe 610 is inserted into the target tissue 120 at the location of the connective fibrous tissue 122. Multiple bursts of laser energy 504, which are from appropriate energy source 102 that matches the transmission bands of fatty tissue 124 and the absorption bands of collagen, are emitted and treat connective fibrous tissue 122 directly. The use of fiber optic delivery systems for laser energy is well known within the industry, but the use of this technique with a selectively absorbing energy source to treat cellulite and adipose tissue is not obvious. Prior attempts to try this have used energy sources that did not distinguish between the collagen and the fat and the result was extensive damage to all the surrounding tissue and a poor cosmetic result. An additional improvement to this percutaneous approach is to use a fiber optic probe 610 that directs the energy out the front or side of the forward or side-firing tip 614. This allows the probe 610 to be placed along side the connective strands 122 under the skin surface 116 and cut in a line with the pulsed energy 504 pointed towards the skin surface 116. In one alternative embodiment, it is also possible to perform this procedure under ultrasound imaging to more accurately locate and treat the connective strands 122, such as those located in the valleys 510 between the dimples of the cellulite and adipose tissue as opposed to those located in the surface tissue 512 of the cellulite tissue. The use of energy in the range of 1.3 μm-1.6 μm or 1.9 μm to 2.2 μm allows the connective tissue 122 to be treated without affecting the surrounding fatty tissue 124. In one embodiment, the use of a more highly absorbing 2.0 μm laser energy 110 such as produced by a Thulium or Holmium doped YAG crystal may be more appropriate as the use of a percutaneous fiber optic makes it unnecessary to optically penetrate the epidermis to reach the target tissue 120.

Figure 10:
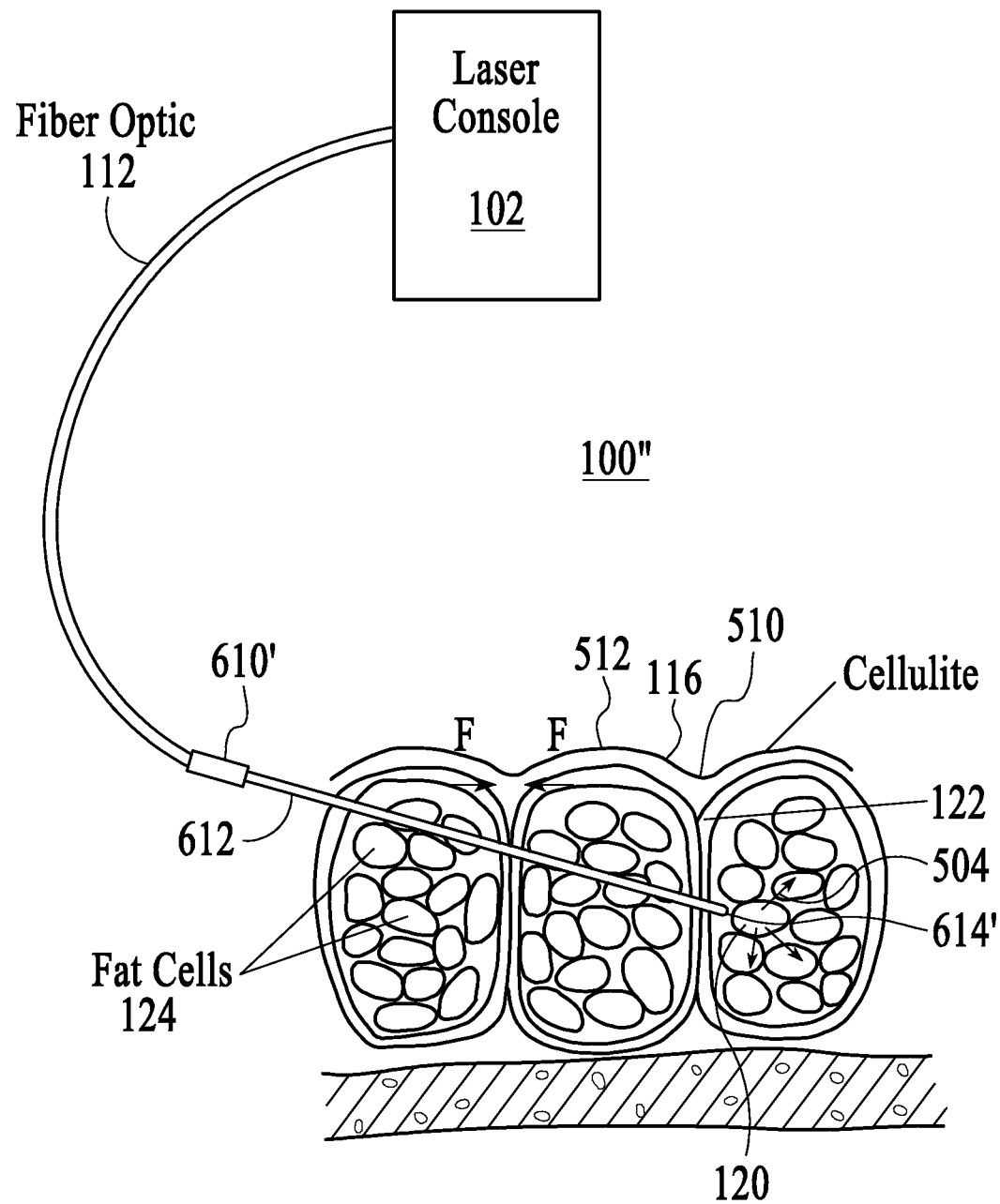
FIG. 10 is a representative detail schematic diagram of another embodiment of the cellulite and adipose tissue treatment system 100" of the present invention.

FIG. 10 is a representative detail schematic diagram of another embodiment of the cellulite and adipose tissue treatment system 100' of the present invention. As shown, the laser energy 110 from the energy source 102 is directed into delivery device 112 which may be a fiber optic, articulated arm, or an electrical cable etc. At the distal end of delivery device 112 is a front fire fiber optic probe 610' for directing the pulsed energy 504 inside the target tissue 120. The front fire fiber optic probe 610' includes a long cannula 612' for easy access and a forward firing tip 614' for safe treatment, which may optionally comprise mechanical breaking of the fibers when in contact.

Figure 11:
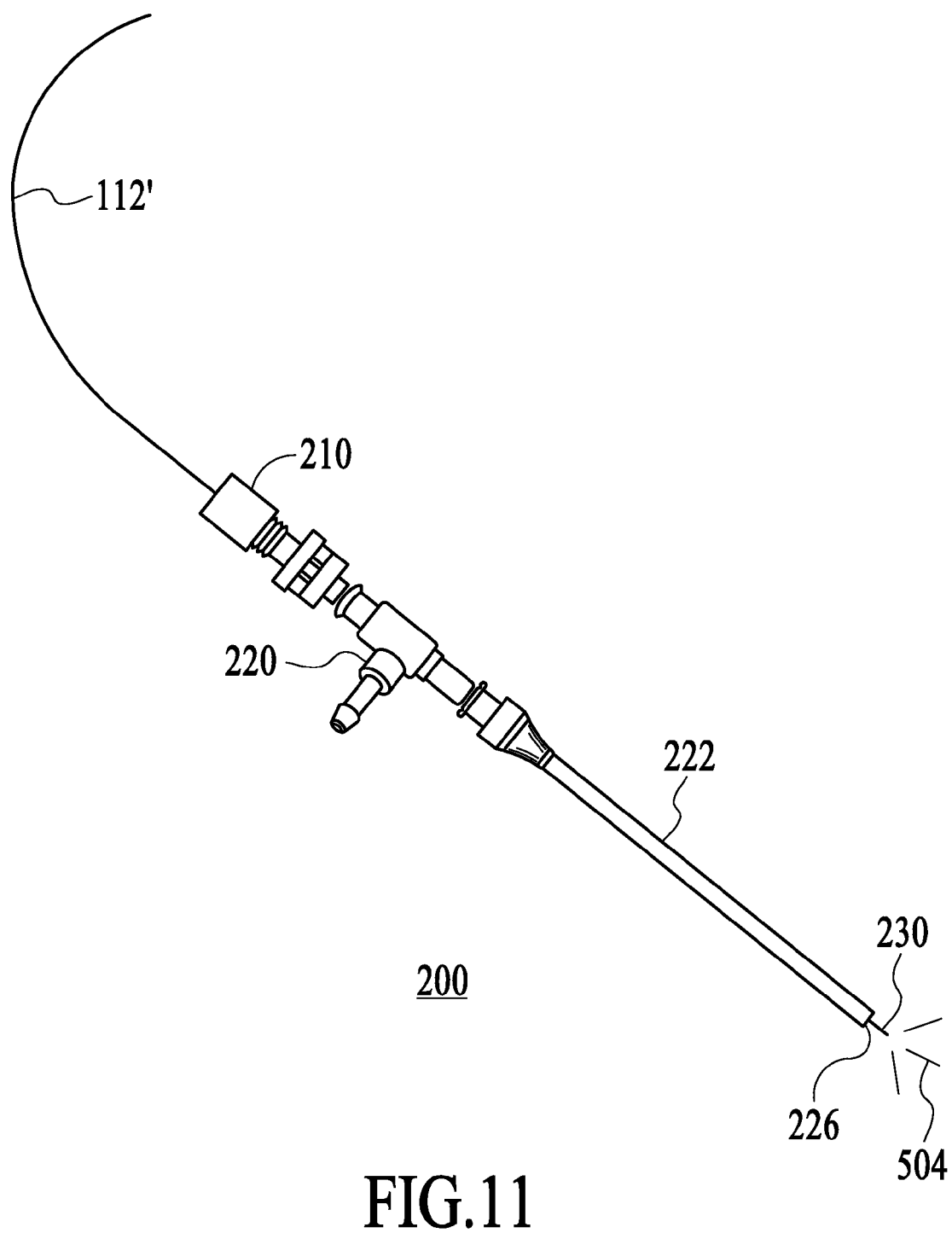
FIG. 11 is a representative detail isometric drawing of an embodiment of the cellulite and adipose tissue treatment system 200 of the present invention.
Figure 12C:
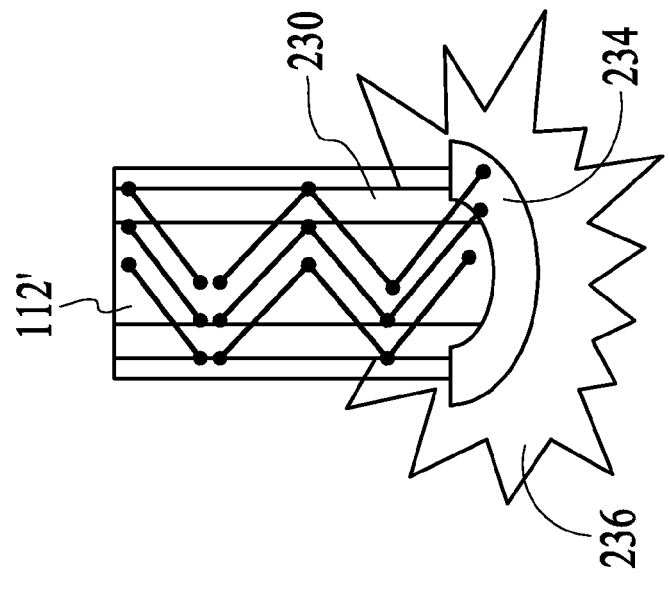
FIGS. 12A, 12B and 12C are representative section views of an embodiment of the firing tip 614' best shown in FIGS. 10 and 11.
Figure 12B:
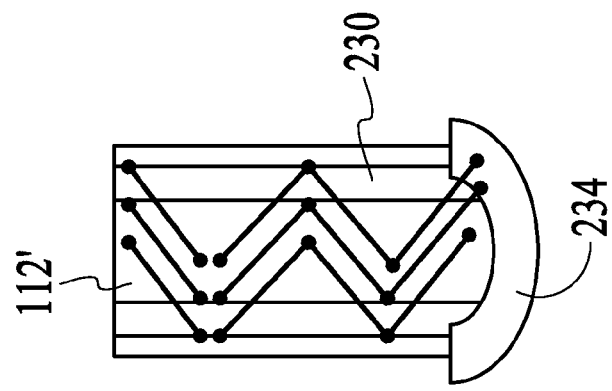
Figure 12A:
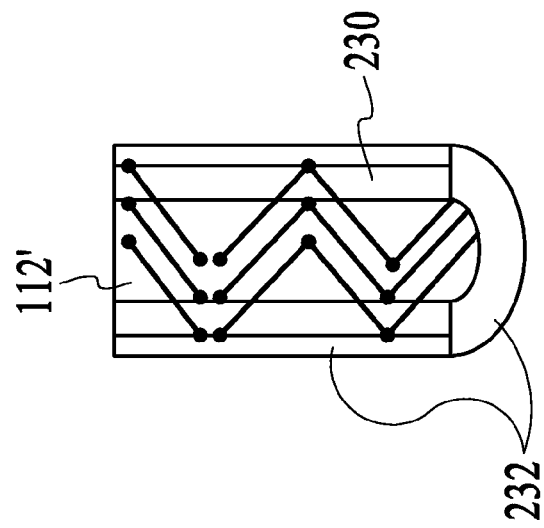

FIG. 11 is a representative detail isometric drawing of an embodiment of the cellulite and adipose tissue treatment system 200 of the present invention. FIGS. 12A, 12B and 12C are representative section views of an embodiment of the firing tip 614' best shown in FIGS. 10 and 11.

As described above with regard to FIG. 10, an embodiment of the front fire fiber optic probe 610' comprises a coated fiber optic laser delivery device 112'. The coated fiber optic 112' is secured into a Touhy Borst or equivalent clamp 210. A side-port 220 is useful for optional aspiration of liquified fat, blood or other tissue. As shown, the Touhy Borst clamp adapter 210 is used to fix the length of the fiber 112' so that the distal tip 230 of the fiber 112' is guaranteed to extend beyond the distal tip 226 of the cannula 222. The Touhy Borst adapter 210 essentially clamps to the fiber 112' to mark proper extension of the fiber tip 230 past the distal end 226 of the cannula 222.

As described above, the present invention is a method for treating cellulite and adipose tissue by moving the distal tip 230 of the optical fiber 112' past the blunt end 226 of the cannula 222 so that heat does not impinge on the blunt end 226 and heat it up. The smooth and blunt end 226 of the cannula 222 prevents inadvertent puncture of skin and is safer overall to use. The apparatus includes a relatively stiff or rigid polyimide coated optical fiber 112', optionally cleaved flat or at an angle, providing the advantage of not requiring the use of the cannula 222 and resistance by the fiber 112' to breakage particularly during placement or use. By extending the firing tip 230 of the fiber optic 112' past the blunt distal end 226 of the cannula 222, the firing tip 230 is well beyond the cannula 222 and there is no risk of overheating the cannula 222.

The cladding 232 of the fiber 112' is not stripped off prior to use. The fiber 112' can be cleaved through the entire coating 232. Thus, laser energy heats the coating 232 creating a carbonized tip 234. Thus, the laser energy goes mostly into heating the tip 230 and directly to target tissue. In one embodiment, the pulsed hot tip laser explodes the tissue and fat without extensive thermal effects. Fat is liquified or ablated, and the pulsed laser creates an explosively hot cutting tip 230.

The fiber coating 232 is made of a material which absorbs the laser energy at the wavelength utilized. During use, it is an advantage to cause the distal end of the coating 232 to burn to a char 234 during laser delivery. The char 234 heats to a very high temperature and acts as a hot tip ablation device, having a hat, ablative cutting surface. In an embodiment of the present invention, the method using a pulsed laser in conjunction with a coated fiber 112' such that the rapid temperature rise at the charred fiber tip 230 causes an acoustic explosion which ablates and disrupts tissue. The pulsed energy ablates a zone 236 of tissue with minimal peripheral or other unintended thermal damage. Photoacoustic ablation is similar to CW Nd:YAG sapphire crystal contact tip technology. The tip 230 requires an "initiation" to enable the carbon char 234 at the distal end 230 of the coated fiber 112' to function as a hot cutting tip. The carbon layer 234 on the tip 230 absorbs laser energy, creating an intense white hot ablation point. The system adds short pulse length pulsed energy to achieve a white hot acoustic ablation mechanism. Thus, ablation of connective tissue occurs at low energy fluences, with resultant minimal collateral damage.

The tip 230 of the coated fiber 112' can be inserted beyond or past the tip 226 of the cannula 222 so that it is no longer adjacent the cannula tip 226, increasing maneuverability and improving the efficiency of the cutting tip 230. Additionally, by moving the distal tip 230 of the optical fiber 112' well past the tip 226 of the cannula 222 there is less chance that the metal cannula 222 will be heated by the laser beam exiting from the emitting face or tip 234 of the fiber 112', it provides an advantage to minimize heating of the tip 226 of the cannula 222 which if heated may cause burns to the patient's skin as it is introduced and/or withdrawn before, during or after use.

It is also possible to use a Touhy Borst clamp 210 on the fiber 112' as a marker during other types of visualization including optical, X-ray, sonic imaging, MRI, CAT-scan or other spectral analysis visualization, to guarantee that the fiber 112' is well beyond the cannula tip 226. Using an aiming beam such as element 137 shown in FIG. 4, up to 10 times or more brighter than the conventional aiming beam, the practitioner can easily determine exactly where the fiber tip 230 is and be able to move it well past the cannula tip 226 before firing it to ablate the undesirable connective tissue.

Fat is very difficult to target using conventional selective photothermolysis. Table 1 shows the optical absorption of laser energy created by an Nd:YAG laser in fat tissue.
Optical Absorption of Nd:YAG Wavelengths:

TABLE 1

| Optical Absorption of Fat | | |
| --- | --- | --- |
| 1064 | Fat = 0.06 | Tissue = 0.14 |
| 1320 | Fat = 0.16 | Tissue = 1.60 |

The treatment of the present invention does not depend upon optical absorption properties of fat.

The pulsed hot tip laser energy explodes tissue and fat without extensive thermal effects. Fat is liquefied, not cooked. Thus, pulsed energy at 1320 nm wavelength ablates very similar to pulsed energy at 1064 nm. Furthermore, 1320 nm also tightens the sub dermal collagen better than energy at 1064 nm.

Table 2 shows a comparison of the collateral tissue damage caused by various types of electromagnetic energy.

TABLE 2

Collateral Tissue Damage

| Device/Wavelength | Power | Depth |
|---|---|---|
| Electrocautery | #4 cut mode | 924 µm |
| Ho:YAG 2.1 µm | 4 Watts | 321 µm |
| $CO_2$ 10.6 µm | 3 Watts | 221 µm |
| Nd:YAG 1.06 µm | 3 Watts | 132 µm |
| Nd:YAG 1.32 µm | 3 Watts | 127 µm |
| Nd:YAG 1.32 µm | 4 Watts | 181 µm |

Table 3 shows the effect of pulse width, ablation width and coagulation width.

TABLE 3

Effect of Pulse Width

| Time | Ablation Width | Coagulation Width |
|---|---|---|
| 120 µsec | 987 µm | 49 µm |
| 500 µsec | 593 µm | 63 µm |
| 1200 µsec | 515 µm | 81 µm |

In conclusion, shorter pulses ablate more tissue with less collateral damage to tissue. Energy at 1320 nm used for acoustic ablation shows less collateral damage than electrocautery, $CO_2$, and Holmium lasers in a pulsed cutting mode. This is the opposite action predicted by non-contact thermal and selective photothermolysis theory. Thus, it has been shown that acoustic ablation is a new mechanism to treat tissue with low absorption. According to the present invention described herein, treatment can be made using a variable pulsed laser that can switch between microsecond ablative pulses and millisecond thermal pulses.

The present invention incorporates U.S. Pat. No. 5,820,626 issued Oct. 13, 1998 to Baumgardner and U.S. Pat. No. 5,976,123 issued Nov. 2, 1999 to Baumgardner et al. herein by reference in their entirety, without limitations, and in particular with regard to their teachings regarding surface cooling of tissue during laser treatment.

Wound Healing and Growth Factors; Mesotherapy and Lipotherapy

When a tissue is injured, polypeptide growth factors, which exhibit an array of biological activities, are released into the wound where they play a crucial role in healing (see, e.g., Hormonal Proteins and Peptides (Li, C. H., ed.) Volume 7, Academic Press, Inc., New York, N.Y. pp. 231 277 (1979) and Brunt et al., Biotechnology 6:25 30 (1988)). These activities include recruiting cells, such as leukocytes and fibroblasts, into the injured area, and inducing cell proliferation and differentiation. Growth factors that may participate in wound healing include, but are not limited to: platelet-derived growth factors (PDGFs); insulin-binding growth factor-1 (IGF-1); insulin-binding growth factor-2 (IGF-2); epidermal growth factor (EGF); transforming growth factor-.alpha. (TGF-.alpha.); transforming growth factor-.beta. (TGF-.beta.); platelet factor 4 (PF-4); and heparin binding growth factors one and two (HBGF-1 and HBGF-2, respectively).

PDGFs are stored in the alpha granules of circulating platelets and are released at wound sites during blood clotting (see, e.g., Lynch et al., J. Clin. Invest. 84:640 646 (1989)). PDGFs include: PDGF; platelet derived angiogenesis factor (PDAF); TGF-.beta.; and PF4, which is a chemoattractant for neutrophils (Knighton et al., in Growth Factors and Other Aspects of Wound Healing: Biological and Clinical Implications, Alan R. Liss, Inc., New York, N.Y., pp. 319 329 (1988)). PDGF is a mitogen, chemoattractant and a stimulator of protein synthesis in cells of mesenchymal origin, including fibroblasts and smooth muscle cells. PDGF is also a nonmitogenic chemoattractant for endothelial cells (see, for example, Adelmann-Grill et al., Eur. J. Cell Biol. 51:322 326 (1990)).

IGF-1 acts in combination with PDGF to promote mitogenesis and protein synthesis in mesenchymal cells in culture. Application of either PDGF or IGF-1 alone to skin wounds does not enhance healing, but application of both factors together appears to promote connective tissue and epithelial tissue growth (Lynch et al., Proc. Natl. Acad. Sci. 76:1279 1283 (1987)).

TGF-.beta. is a chemoattractant for macrophages and monocytes. Depending upon the presence or absence of other growth factors, TGF-.beta. may stimulate or inhibit the growth of many cell types.

Other growth factors, such as EGF, TGF-.alpha., the HBGFs and osteogenin are also important in wound healing. Topical application of EGF accelerates the rate of healing of partial thickness wounds in humans (Schultz et al., Science 235:350 352 (1987)). Osteogenin, which has been purified from demineralized bone, appears to promote bone growth (see, e.g., Luyten et al., J. Biol. Chem. 264:13377 (1989)). In addition, platelet-derived wound healing formula, a platelet extract which is in the form of a salve or ointment for topical application, has been described (see, e.g., Knighton et al., Ann Surg. 204:322 330 (1986)).

The heparin binding growth factors (HBGFs), including the fibroblast growth factors (FGFs), which include acidic HBGF (aHBGF also known as HBFG-1 or FGF-1) and basic HBGF (bHBGF also known as HBGF-2 or FGF-2), are potent mitogens for cells of mesodermal and neuroectodermal lineages, including endothelial cells (see, e.g., Burgess et al., Ann Rev. Biochem. 58:575 606 (1989)). In addition, HBGF-1 is chemotactic for endothelial cells and astroglial cells. Both HBGF-1 and HBGF-2 bind to heparin, which protects them from proteolytic degradation. The array of biological activities exhibited by the HBGFs suggests that they play an important role in wound healing.

Basic fibroblast growth factor (FGF-2) is a potent stimulator of angiogenesis and the migration and proliferation of fibroblasts (see, for example, Gospodarowicz et al., Mol. Cell. Endocinol. 46:187 204 (1986) and Gospodarowicz et al., Endo. Rev. 8:95 114 (1985)). Acidic fibroblast growth factor (FGF-1) has been shown to be a potent angiogenic factor for endothelial cells (Burgess et al., supra, 1989). Other FGF's may be chemotactic for fibroblasts. Growth factors are, therefore, potentially useful for specifically promoting wound healing and tissue repair.

"HBGF-1," which is also known to those of skill in the art by alternative names, such as endothelial cell growth factor (ECGF) and FGF-1, as used herein, refers to any biologically active form of HBGF-1, including HBGF-1.beta., which is the precursor of HBGF-1.alpha. and other truncated forms, such as FGF. U.S. Pat. No. 4,868,113 to Jaye et al., herein incorporated by reference, sets forth the amino acid sequences of each form of HBGF. HBGF-1 thus includes any biologically active peptide, including precursors, truncated or other modified forms, or mutants thereof that exhibit the biological activities, or a subset thereof, of HBGF-1.

Two substances commonly used in injections to "dissolve" fat are phosphatidylcholine (PPC) and sodium deoxycholate.

The present invention utilizes multiple sessions and many injections of the chemicals. Mesotherapy is a more general term for a variety of minimally invasive techniques in which different medications are directly injected into the skin and the layer beneath the skin for many reasons including musculoskeletal problems, neurological problems and cosmetic conditions. Lipodissolve or lipotherapy, or several other terms, refers specifically to the treatment of fat deposits thru injections.

Other growth factors, mesotherapy and lipotherapy drugs may also be known to those of skill in the art by alternative nomenclature. Accordingly, reference herein to a particular growth factor by one name also includes any other names by which the factor is known to those of skill in the art and also includes any biologically active derivatives or precursors, truncated mutant, or otherwise modified forms thereof.

U.S. Pat. No. 7,094,252 issued Aug. 22, 2006 entitled ENHANCED NONINVASIVE COLLAGEN REMODELING, U.S. Pat. No. 7,217,265 issued May 15, 2007 entitled TREATMENT OF CELLULITE WITH MID-INFRARED RADIATION, and U.S. patent application Ser. No. 11/612,324 filed Dec. 18, 2006 entitled ENDOVENOUS LASER TREATMENT GENERATING REDUCED BLOOD COAGULATION, are all incorporated herein by reference in their entireties.

Unless defined otherwise, all technical and scientific terms used herein have the same meaning as commonly understood by one of ordinary skill in the art to which the present invention belongs. Although any methods and materials similar or equivalent to those described can be used in the practice or testing of the present invention, the methods and materials are now described. All publications and patent documents referenced in the present invention are incorporated herein by reference.

While the principles of the invention have been made clear in illustrative embodiments, there will be immediately obvious to those skilled in the art many modifications of structure, arrangement, proportions, the elements, materials, and components used in the practice of the invention, and otherwise, which are particularly adapted to specific environments and operative requirements without departing from those principles. The appended claims are intended to cover and embrace any and all such modifications, with the limits only of the true purview, spirit and scope of the invention.

We claim:

1. A device for the percutaneous treatment of cellulite and adipose tissue with laser energy, the device comprising:
    a hollow cannula with a blunt, non-piercing tip at a distal end for placement underneath the skin of a patient, said hollow cannula having an opening at the distal end;
    a variable pulse length laser source having emitting characteristics for generating a laser beam that causes the ablation of undesirable connective tissue;
    a coated optical fiber having a coated distal firing tip for absorbing laser energy to heat the firing tip of the fiber, the optical fiber connected to said variable pulse length laser source and movably disposed within the hollow cannula to convey the laser beam from said source to the distal firing tip positioned at a point substantially beyond the distal, blunt tip end of the cannula to minimize heating of the blunt tip end of the cannula; and
    a Touhy-Borst or equivalent clamp used to fix the length of the optical fiber so that the distal firing tip of the optical fiber can be set past the distal end of the cannula.

2. The device of claim 1 wherein said variable pulse length laser source emits at a wavelength between about 1.3 um and about 1.6 um.

3. A device for the percutaneous treatment of cellulite and adipose tissue with laser energy, the device comprising:
    a hollow cannula with a blunt, non-piercing tip at a distal end for placement underneath the skin of a patient, said hollow cannula having an opening at the distal end;
    a laser source having emitting characteristics for generating a laser beam that causes the ablation of undesirable connective tissue;
    a coated optical fiber having a coated distal firing tip for absorbing laser energy to heat the firing tip of the fiber, the optical fiber connected to said laser source and movably disposed within the hollow cannula to convey the laser beam from said source to the distal firing tip positioned at a point substantially beyond the distal, blunt tip end of the cannula to minimize heating of the blunt tip end of the cannula;
    a Touhy-Borst or equivalent clamp used to fix the length of the optical fiber so that the distal firing tip of the optical fiber can be set past the tip at the distal end of the cannula; and
    an injector mechanism for delivery of compounds such as for wound healing compounds meseotherapy and lipotherapy or lipodissolve drugs to the treatment site through the hollow cannula.

* * * * *